United States Patent [19]

Guadagno

[11] Patent Number: 4,742,002
[45] Date of Patent: May 3, 1988

[54] TEST KIT AND METHOD FOR DETERMINING THE PRESENCE OF BLOOD IN A SPECIMEN AND FOR TESTING THE EFFECTIVENESS OF PEROXIDASE INACTIVATING SOLUTION

[75] Inventor: Philip A. Guadagno, Vidor, Tex.

[73] Assignee: Helena Laboratories Corporation, Beaumont, Tex.

[21] Appl. No.: 571,254

[22] Filed: Jan. 16, 1984

[51] Int. Cl.4 ............................................. C12Q 1/28
[52] U.S. Cl. ........................................ 435/28; 436/66; 435/184; 435/810
[58] Field of Search .................. 436/66; 435/28, 184, 435/805, 810

[56] References Cited

U.S. PATENT DOCUMENTS 4,541,987 9/1985 Guadagno ............................ 436/66

Primary Examiner—Sam Rosen
Attorney, Agent, or Firm—Cullen, Sloman, Cantor, Grauer, Scott & Rutherford

[57] ABSTRACT

A test kit for determining the presence of occult blood is disclosed which includes an improved monitor system having a reagent test area including a metal salt with an oxidation potential sufficient to catalyze a chromogen reaction in the guaiac impregnated paper when exposed to a peroxide developing solution. A peroxidase inactivating test area is provided for verifying the effectiveness of a peroxidase inactivating solution comprising guanidine hydrochloride and ethylenediaminetetraacetic acid. An improved method of testing occult blood is also disclosed wherein a peroxidase inactivating solution is applied to a monitor and a sample area just prior to application of the developing solution.

12 Claims, 2 Drawing Sheets

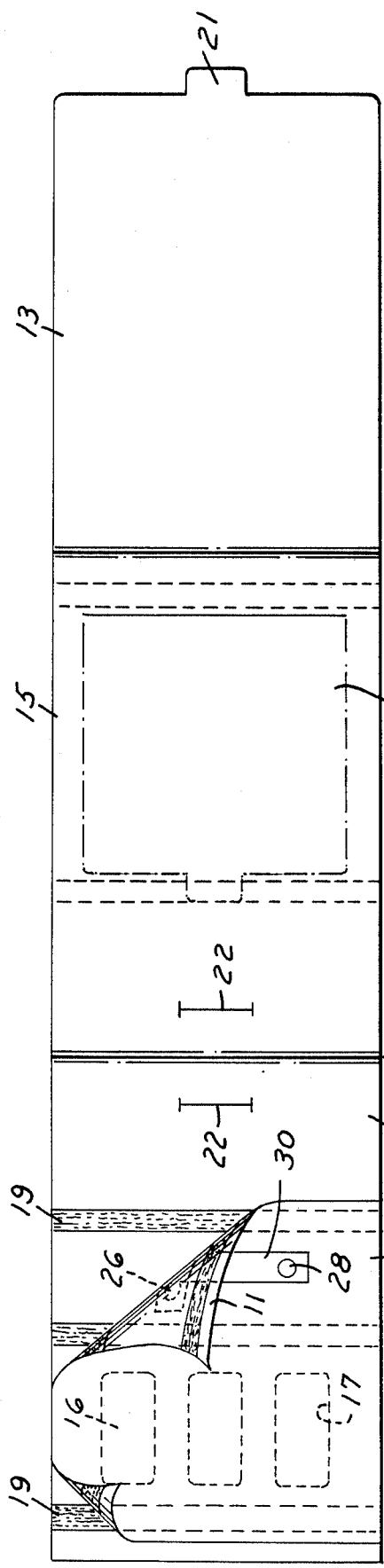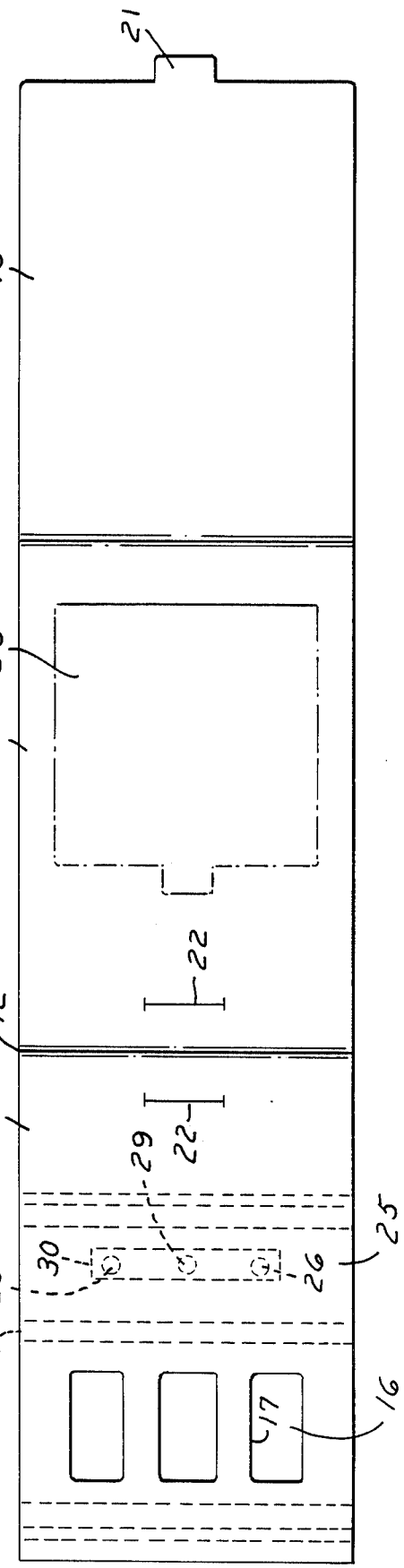

TEST KIT AND METHOD FOR DETERMINING THE PRESENCE OF BLOOD IN A SPECIMEN AND FOR TESTING THE EFFECTIVENESS OF PEROXIDASE INACTIVATING SOLUTION

BACKGROUND OF THE INVENTION

1. Technical Field

The present invention relates to a method and test kit, or test slide, for sensing the presence of blood in stool specimens. More specifically, the present invention relates to an improved test slide incorporating test monitors for verifying the results of the test and for checking the effectiveness of a vegetable peroxidase denaturing solution.

2. Prior Art

Test slides or kits for determining the presence of blood in stool samples are useful in the early diagnosis of cancer of the digestive tract. Such test slides provide a convenient method by which a patient may send a stool specimen to a laboratory for analysis.

One form of such a test slide is disclosed in U.S. Pat. No. 3,996,006 to Pagano in which a test slide comprising a guaiac impregnated paper is enclosed in a multifolded cardboard package having test areas which are accessible through a set of cardboard flaps formed in the top of the test slide. A patient using the test slide smears a small sample of a stool specimen on each of the test areas, closes the flaps and sends the test slide to a laboratory for analysis. When the test slide is received at the laboratory, a technician opens a flap in the bottom of the test slide to obtain access to the other side of the guaiac impregnated paper. The technician then applies a hydrogen peroxide developing solution to the guaiac impregnated paper. If occult blood is present in the sample, the blood will catalyze a chromogen reaction in the guaiac when exposed to the developing solution. If no blood is present in the sample the chromogen reaction should not occur and the test result would be negative.

To provide a check on the performance of the test reagent and developer solution U.S. Pat. No. 4,365,970 to Lawrence et al discloses the concept of imprinting a portion of the test slide bearing the test reagent with a small quantity of hemoglobin or hemin, a hemoglobin derived catalyst which reacts to adverse environmental conditions in a manner similar to hemoglobin. When the test slide is exposed to the developing solution the hemoglobin or hemin will normally cause the guaiac in that portion of the test slide to undergo the chromogen reaction as long as the guaiac and developing solution are performing properly and the hemoglobin or hemin has not decomposed or been denatured.

The use of hemoglobin or a derivative of hemoglobin, such as hemin, presents certain problems in the manufacture of test slides. Hemoglobin is an organic substance which is subject to decomposition or denaturation. A problem with use of a hemoglobin derivative is the danger of transmitting a venereal disease, hepatitis or another communicable disease capable of being transmitted with a blood sample. To reduce the risk of transmitting such a disease it has been necessary to test the hemoglobin or hemin prior to sending it to a printer to verify that no disease is carried by the substance.

Current scientific research suggests that the ingestion of foods including vegetable peroxidase may cause false indications of blood in a stool sample. After digestion of food including vegetable peroxidase is complete a certain residual amount of vegetable peroxidase is passed through the intestines and is included in the stool specimen. A solution to the problem proposed in U.S. Pat. No. 4,333,734 to Fleischer is to inactivate the vegetable peroxide by applying a denaturing, or inactivating, solution to the test slide prior to development. While this makes occult blood test slides more reliable, there is no way disclosed for determining whether the inactivating solution is effective in inhibiting the catalyzation of the guaiac by the residual vegetable peroxidase in the stool specimen.

If the test spot of Lawrence were used and a positive result was indicated by the test, it would not be possible to determine whether the positive result was caused by vegetable peroxidase or occult blood in the sample. In the event the vegetable peroxidase inhibiting solution is not effective, it would be possible to have a false positive test result caused by the presence of vegetable peroxidase which had not been neutralized. If a false positive test occurs, a patient may be subjected to unnecessary tests.

These and other problems encountered in using prior art test slides have been overcome according to the present invention.

SUMMARY OF THE INVENTION

The present invention relates to a method including the use of a test kit, or test slide, having an improved control area for verifying the effectiveness of a vegetable peroxidase inactivating solution, a guaiac test reagent and a peroxide developing solution.

The reagent test area, or positive monitor, is provided for checking the effectiveness of a test reagent and developing solution. The positive monitor may comprise a deposit of metal salt which is selected from a group of metal salts having an oxidation potential sufficient to catalyze a reaction in the chromogenic test reagent when a developing solution is applied to the test area. The positive monitor only catalyzes the test reagent on the test slide in the presence of a developing solution if the test reagent and developing solution are both functional. A metal salt may be chosen which is more resistant to decomposition than hemoglobin under specified conditions. Alternatively, a positive monitor comprising a deposit of peroxidase may be provided that will work in the same way as the metal salt.

The positive monitor of the present invention is not based upon hemoglobin or a blood derivative and therefore eliminates the need to test the test monitor substance for communicable diseases as is required with positive monitors including a hemoglobin derivative.

The present invention also relates to the provision of a peroxidase inactivating test area to determine the effectiveness of a vegetable peroxidase inactivating solution. If the test procedure calls for a vegetable peroxidase inactivating wash there is a need to assure the effectiveness of the vegetable peroxidase inactivating solution. The purpose of the peroxidase inactivating test area is to reduce the chance that the guaiac will be catalyzed by the residual vegetable peroxidase in the sample if the vegetable peroxidase inactivating solution is not functioning.

According to the present invention a vegetable peroxidase inactivating monitor may simply be provided by including a deposit of the chromogen reagent and a peroxidase material in a location spaced from the sample test area on the test slide. The peroxidase material is preferably a vegetable peroxidase similar to that appearing in human stool specimens. If the vegetable peroxidase inactivating solution is effective, the vegetable peroxidase monitor will be inactivated when the developing solution is applied to the test slide and there will be no change or no indication in the monitor spot. However, if the vegetable peroxidase inactivating solution is ineffective the vegetable peroxidase monitor will undergo the chromogen reaction. This will warn the laboratory technician performing the test to either ignore the test result or at least repeat treatment of the sample area with a new vegetable peroxidase inhibiting solution.

The method of the present invention is as simple to use as prior art methods and provides verification of the effectiveness of the test reagent and developing solution by means of the positive monitor and also provides a method of verifying the effectiveness of the vegetable peroxidase inactivating solution by the provision of the vegetable peroxidase monitor on the test slide.

These and other advantages and improvements realized by the present invention will be more fully understood upon studying the drawings and with reference to the following detailed description.

BRIEF DESCRIPTION OF THE DRAWINGS

FIG. 4 is an inside view of the test slide blank showing the means by which the test slide is attached to the package.

FIG. 5 is an outside view of the package blank.

DETAILED DESCRIPTION

Figure 1:
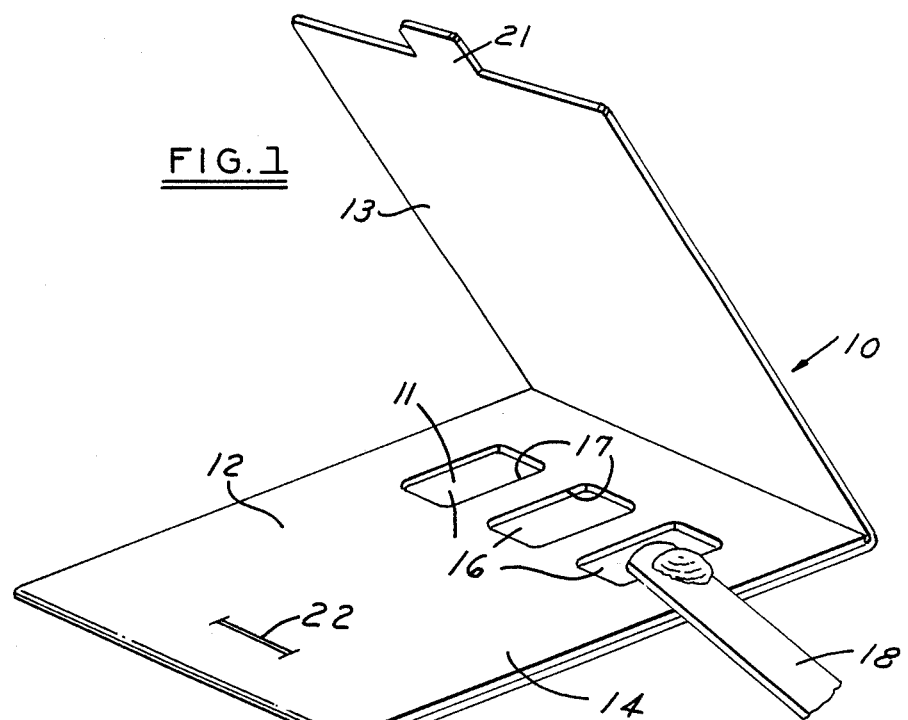
FIG. 1 is a perspective view of the top side of the test slide as it is opened by a patient to apply a sample of a stool specimen to the test slide.
Figure 2:
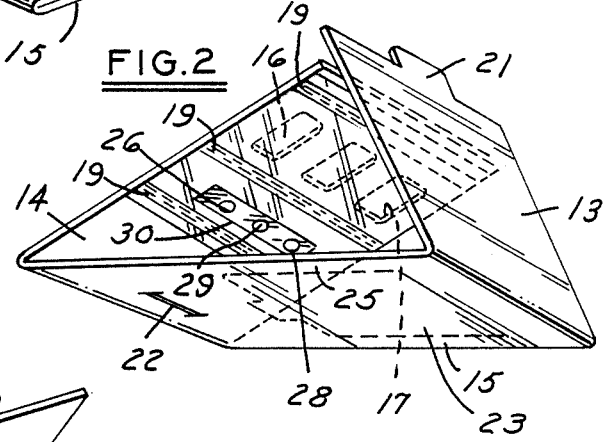
FIG. 2 is a perspective view showing the pattern of folding employed to assemble the package and test slide.
Figure 3:
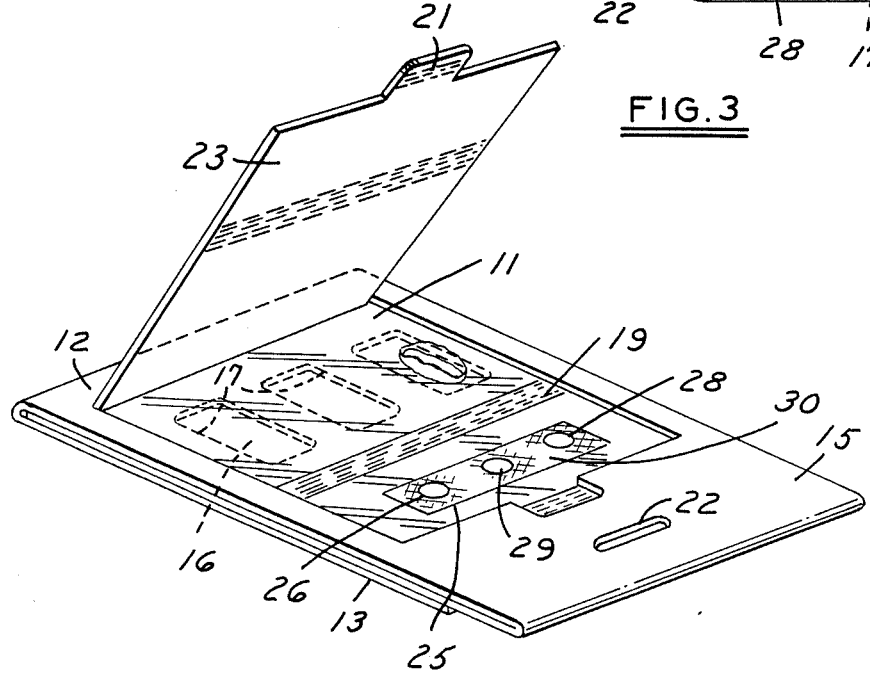
FIG. 3 is a perspective view of the bottom of the test slide opened for analysis by the laboratory technician.

Referring now to the drawings, a test kit 10 is shown to include a slide 11 enclosed in a package 12. The slide 11 is preferably made from an absorbant paper and is treated, impregnated or imprinted with a test reagent, preferably guaiac, which is capable of undergoing a chromogen reaction. The package 12 includes a cover panel 13 which is folded over a test slide support panel 14. A back plate 15 is folded over and secured to the opposite side of the test slide support panel 14 from the cover 13.

The test slide support panel 14 defines one or more sample test areas 16 by the formation of one or more openings 17 in the test slide support panel 14. The test slide 11 is secured to the test slide support panel 14 preferably on the side opposite the cover 13 by glue strips 19. Samples of a feces specimen are applied to each of the sample test areas 16 with an applicator stick 18. After the samples have been applied to the sample test area 16 the cover 13 is closed and secured to the test slide support panel 14 by means of the tab 21 on the cover 13 being inserted in the thumbcut 22 formed through the test slide support panel 14 and the back plate 15. The cover 13 is thereby securely maintained in position covering the sample test area 16. The test kit 10 is then sent to a laboratory for analysis of the test slide 11.

When received in the laboratory, the package 12 is opened by separating a flap 23 formed by die cut perforation in the back plate 15 to expose the opposite side of the test slide 11 from where the sample was applied. A first portion including the sample test areas 16 and a second portion including a control area 25 on the test slide 11 are both exposed when the flap 23 is lifted.

The second portion of the test slide includes a reagent test area 26 and a peroxidase inactivating test area 28 that are separated from each other in the sample test area by a hydrophobic barrier 30. The hydrophobic barrier 30 may be made of an organic soluble compound such as a mixture of tolulene and parafin which is applied to the test slide by stamping or printing. Alternatively, a negative monitor area 29 consisting of the test reagent such as guaiac may be defined by the hydrophobic barrier 30. If a catalyst-contaminent is present in area 29, it will cause a blue color change as a result of the oxidation of the guaiac in the presence of a peroxide solution. If no catalyst is present, no color change will occur.

The control area 25 includes one or more test areas for checking the effectiveness of the reagents carried by the test slide 11 and the solutions applied to the test slide 11 by a laboratory technician.

The effectiveness of the guaiac and developing solution is checked by applying developing solution to the reagent test area 26 at the same time it is applied to the sample. The reagent test area including a printed deposit of a non-hemoglobin catalyst which should always cause the oxidation of the guaiac and the presence of a peroxide solution. Thus, the reagent test area checks both the guaiac and the peroxide solution to prevent false negative test results.

In accordance with the present invention a reagent test area 26 is provided which does not use hemoglobin derivative to monitor reagent performance. In the disclosed embodiment, the reagent test area 26 has one or more metal salts having an oxidation potential sufficient to catalyze a reaction in the chromogen reagent.

Several metal salts suitable for use in the test kit of the present invention comprise appropriate salts of lead, copper, calcium, iron and nickel and may also comprise hypochlorite solutions and peroxidase. Other metal salts currently under evaluation are also believed to be usable in the test kit of the present invention.

Examples of two different solutions used to create monitors having desirable sensitivity and resistance to denaturation by environmental conditions during shipping and handling are as follows:

EXAMPLE 1

An eight gram percent solution of lead acetate ($Pb(C_2H_3O_2)_2 \cdot 3H_2O$) in glycerol ($C_3H_5(OH)_3$) is first prepared. The lead acetate/glycerol solution is then combined with a water base varnish at a ratio by volume of 1 to 9. The lead acetate/glycerol solution and water base varnish are thoroughly mixed. The mixture is now suitable for use in printing with traditional or modified offset printing equipment directly on the guaiac impregnated test slide.

EXAMPLE 2

A copper cyanide monitor may be prepared by mixing two grams of potassium cyanide (KCN) and one gram of copper sulfate pentahydrate ($CuSO_4 \cdot 5H_2O$). The above mixture is then dissolved in 25 milliliters of water to form a copper cyanide (CuCN) solution. The copper cyanide solution is then mixed with a water based varnish by combining 100 milliliters of copper cyanide solution and 900 milliliters of water base varnish and thoroughly mixed. The varnish mixture is ready for printing on guaiac impregnated paper.

The above examples are not intended to be limiting but are merely illustrative of the invention. The water base varnish used in the above examples may be OP varnish, a product distributed by I.P.I. Printing Inks.

Another improvement in the monitoring system provided in accordance with the present invention is the inclusion of a peroxidase inactivating test area 28 comprising a deposit of peroxidase on a portion of the test slide spaced from the sample test areas 16.

While it was disclosed in U.S. Pat. No. 4,333,734 to Fleischer to treat a test slide with a solution of guanidine hydrochloride (NHC(NH$_2$)$_2$.HCl) and ethylenediaminetetraacetic acid (EDTA) to prevent peroxidase activity from resulting in false positive tests, the process disclosed in Fleischer requires an extended drying down or waiting period of between two and three hours prior to finishing the developing process.

In experiments with the peroxidase inactivating test area it surprisingly has been found that if a vegetable peroxidase inactivating solution of guanidine hydrochloride and EDTA are combined at a ratio of 2:1 in the same bottle and applied to the slide, the developer may be immediately applied to the test slide without a drying down or waiting period. Since the spot of peroxidase is located on a portion of the same test slide, it is a simple matter to determine that the vegetable peroxidase inactivating solution is effective and there is an immediate indication that any peroxidase in the sample has also been neutralized. Without a peroxidase inactivating test area 28 it would not be possible to immediately develop the sample since there would be no assurance that the vegetable peroxidase inactivating solution was effective.

To analyze the slide, the laboratory technician applies a vegetable peroxidase inactivating solution to both the first and second portions of the test slide to prevent false positive tests caused by the inclusion of vegetable peroxidase in the sample. The vegetable peroxidase inactivating solution is a solution of guanidine hydrochloride which cleaves the protein's hydrogen bonds within the vegetable peroxidase and chelates calcium and magnesium ions with the EDTA in the solution. If a peroxidase based reagent test area 26 is provided, as described above, the laboratory technician will avoid applying the inactivating solution to the reagent test area to be assured of a positive reaction in that area when the developing solution is applied.

The laboratory technician may then develop the slides by applying a peroxide solution to the peroxidase inactivating test area 28 to check the effectiveness of the inactivating solution on the vegetable peroxidase in the monitor. If the developing solution does not yield the characteristic blue color of a guaiac chromogen reaction, the peroxide developing solution may be applied to the sample test area 16 with the assurance that any interfering vegetable peroxidase will have been inactivated.

The improved reagent test area 26 of the present invention provides valuable cross-checking of both the vegetable peroxidase inactivating solution, the guaiac and the peroxide developer which in combination provide an improved test system. The above embodiments are intended as being illustrative of the invention and the scope of the invention should only be interpreted with reference to the following claims.

I claim:

1. A test kit for determining the presence of blood in a specimen comprising slide means for receiving a sample of the specimen in at least one sample test area thereof, and a second peroxidase inactivating solution test area formed on said slide with means on said slide having a deposit of chromogen reagent and peroxidase in a location spaced from the sample test area to test the effectiveness of a peroxidase inactivating solution.

2. The test kit of claim 1 wherein said peroxidase is vegetable peroxidase.

3. The test kit of claim 1 wherein a vegetable peroxidase inactivating solution is applied to the sample test area and the peroxidase inactivating solution test area.

4. The test kit of claim 1 wherein said peroxidase inactivating solution is a solution of guanidine hydrochloride and ethylenediaminetetraacetic acid.

5. The test kit of claim 4 wherein said solution of guanidine hydrochloride and ethylenediaminetetraacetic acid are combined at a ratio of 2:1.

6. A method of determining the presence of blood in a specimen with a test slide carrying a test reagent comprising:
   applying a sample of the specimen to be tested on a first portion of the test slide, said test slide having a deposit of peroxidase in a second portion thereof;
   washing the first and second portions with a peroxidase inactivating solution; and
   applying a developing solution to the first and second portions which will cause blood in the specimen to catalyze a chromogen reaction in the test reagent and will only cause the peroxidase in the second portion to catalyze a chromogen reaction in the test reagent if the peroxidase inactivating solution is ineffective.

7. The method of claim 6 wherein said peroxidase in the second portion is a vegetable peroxidase.

8. The method of claim 6 wherein said test slide has a reagent test area in a third portion comprising a deposit of a metal salt with an oxidation potential sufficient to catalyze a chromogen reaction in the test reagent when said developing solution is applied to the test slide.

9. The method of claim 6 wherein the test slide has a deposit of lead acetate on a third portion spaced from the first portion which will catalyze a chromogen reaction in the test reagent unless either the test reagent or developing solution are not functioning.

10. The method of claim 6 wherein the test slide has a deposit of copper cyanide on a third portion spaced from the first portion which will catalyze a chromogen reaction in the test reagent unless either the test reagent or developing solution are not functioning.

11. The method of claim 6 wherein a plurality of samples are applied at a plurality of spaced locations on the first portion of the test slide to permit a plurality of samples to be tested simultaneously.

12. The method of claim 6 wherein the peroxidase inactivating solution is a solution of guanidine hydrochloride and ethylenediaminetetraacetic acid.

* * * * *